United States Patent
Pflüger et al.

(10) Patent No.: US 11,579,060 B2
(45) Date of Patent: Feb. 14, 2023

(54) METHOD AND DEVICE FOR MEASURING FAT IN MILK

(71) Applicant: Endress+Hauser Flowtec AG, Reinach (CH)

(72) Inventors: Stefan Pflüger, Munich (DE); Wolfgang Drahm, Erding (DE); Hao Zhu, Freising (DE)

(73) Assignee: Endress+Hauser Flowtec AG, Reinach (CH)

( * ) Notice: Subject to any disclaimer, the term of this patent is extended or adjusted under 35 U.S.C. 154(b) by 374 days.

(21) Appl. No.: 16/956,940

(22) PCT Filed: Dec. 10, 2018

(86) PCT No.: PCT/EP2018/084185
§ 371 (c)(1),
(2) Date: Jun. 22, 2020

(87) PCT Pub. No.: WO2019/121109
PCT Pub. Date: Jun. 27, 2019

(65) Prior Publication Data
US 2021/0003491 A1 Jan. 7, 2021

(30) Foreign Application Priority Data
Dec. 22, 2017 (DE) .................. 10 2017 131 269.2

(51) Int. Cl.
*G01N 9/00* (2006.01)
*G01N 22/00* (2006.01)
(Continued)

(52) U.S. Cl.
CPC ............. *G01N 9/002* (2013.01); *G01F 1/74* (2013.01); *G01F 1/8436* (2013.01);
(Continued)

(58) Field of Classification Search
CPC ........ G01N 9/002; G01N 33/06; G01N 22/00; G01F 1/74; G01F 1/8436; G01F 1/8468; G01K 13/02; G01K 13/026; G01L 19/00
See application file for complete search history.

(56) References Cited

U.S. PATENT DOCUMENTS 5,103,181 A * 4/1992 Gaisford ............ G01N 33/2823
324/645
6,147,502 A * 11/2000 Fryer ..................... G01N 22/00
324/636

(Continued)

FOREIGN PATENT DOCUMENTS

| CN | 1853088 A | 10/2006 |
|---|---|---|
| CN | 1934425 A | 3/2007 |

(Continued)

OTHER PUBLICATIONS

Markel, Vadim A., Introduction to the Maxwell Garnett approximation: tutorial, Journal of the Optical Society of America A, vol. 33, No. 7, Jul. 2016, 13 pp.

*Primary Examiner* — Alexander Satanovsky
*Assistant Examiner* — Lynda Dinh
(74) *Attorney, Agent, or Firm* — Mark A. Logan; Endress+Hauser (USA) Holding, Inc.

(57) ABSTRACT

Disclosed is a method for determining of fat content of milk having variable solids fractions and flowing with variable gas content in a pipeline. The method includes ascertaining a velocity of sound and an average density value for the milk based on eigenfrequencies of at least two bending oscillation wanted modes of measuring tubes of a densimeter arranged in the pipeline. The method further includes ascertaining a static pressure in the pipeline; a gas volume fraction based on the velocity of sound; the average density; the pressure; a density of the milk without gas content based on the average density and the gas volume fraction; and a permit- (Continued)

tivity of the milk based on a propagation velocity and/or an absorption of microwaves in the milk. The fat fraction is calculated based on the density of the milk without gas content and on the effective permittivity.

10 Claims, 2 Drawing Sheets

(51) Int. Cl.
| | |
|---|---|
| *G01N 33/06* | (2006.01) |
| *G01F 1/74* | (2006.01) |
| *G01F 1/84* | (2006.01) |
| *G01L 19/00* | (2006.01) |
| *G01K 13/02* | (2021.01) |

(52) U.S. Cl.
CPC ........... *G01F 1/8468* (2013.01); *G01K 13/02* (2013.01); *G01L 19/00* (2013.01); *G01N 22/00* (2013.01); *G01N 33/06* (2013.01); *G01K 13/026* (2021.01)

(56) References Cited

U.S. PATENT DOCUMENTS

| | | | |
|---|---|---|---|
| 7,155,971 B2 * | 1/2007 | Wamhof | .................. A01J 5/00 |
| | | | 73/227 |
| 7,363,800 B2 * | 4/2008 | Gysling | ............. G01N 33/2823 |
| | | | 73/19.01 |
| 2004/0060365 A1 * | 4/2004 | Crudge | ................... G01F 1/712 |
| | | | 73/861 |
| 2016/0313259 A1 | 10/2016 | Shayovitz | |

FOREIGN PATENT DOCUMENTS

| | | | |
|---|---|---|---|
| CN | 101076721 A | | 11/2007 |
| CN | 101336364 A | | 12/2008 |
| CN | 102187187 A | | 9/2011 |
| CN | 102246008 A | | 11/2011 |
| CN | 104704351 A | | 6/2015 |
| CN | 204439543 U | | 7/2015 |
| CN | 107110678 A | | 8/2017 |
| DE | WO 2007/074055 | * | 7/2007 |
| EP | 2026042 A1 | | 2/2009 |
| WO | 9004167 A1 | | 4/1990 |

* cited by examiner

METHOD AND DEVICE FOR MEASURING FAT IN MILK

CROSS-REFERENCE TO RELATED APPLICATIONS

The present application is related to and claims the priority benefit of German Patent Application No. 10 2017 131 269.2, filed on Dec. 22, 2017 and International Patent Application No. PCT/EP2018/084185, filed on Dec. 10, 2018 the entire contents of which are incorporated herein by reference.

TECHNICAL FIELD

The present invention relates to a method and to a device for milk fat measurement:

BACKGROUND

Milk and intermediates won therefrom can be described as mixtures of various components, mainly water, milk fat and solids, wherein the solids comprise essentially proteins, carbohydrates (among these especially lactose) and, in small amounts, minerals.

During the processing chain beginning with raw milk and extending to the manufacture of milk products, the percentages of these components are important parameters for controlling the processes, for process- and quality checking, and for balancing product streams. Usual practice is to determine the percentages using laboratory samples and standard methods. This means that only a few samples can be evaluated, and an analytical result is obtained only with significant delay following the sample taking.

A process-near spectroscopic analysis in the infrared region with automated sample taking is, indeed, possible, however, this is, firstly, very costly and, second, only based on the low volume of the samples taken in comparatively large time intervals. For process control, such an analysis is, consequently, only conditionally suitable.

A density measurement, e.g. by means of Coriolis flowmeter, is, indeed, suitable as inline measuring for continuous process monitoring, and can also be used for determining the fat content, or the solids percentages, of milk when the assumption of a given ratio of the solids percentages of fat, carbohydrates (especially lactose), proteins, etc. is justified. With declining validity of this assumption, the measuring result becomes correspondingly inaccurate.

Another difficulty with the determining of fat content with a Coriolis flowmeter results from microbubbles of air distributed in the milk, which, on the one hand, lessen the effective density and, on the other hand, due to oscillations of the now compressible milk compared with the measuring tube, lead to changed relationships between eigenfrequencies of the oscillating measuring tubes of the flowmeter and the density of the measured substance in the measuring tubes. The limited suitability of Coriolis mass flowmeters for determining the composition of liquids containing gas is described, for example, in U.S. Pat. No. 7,363,800 B2. This teaches an arrangement with, firstly, a microwave sensor for ascertaining dielectric parameters of a medium, second a Coriolis mass flowmeter, third an independent sensor for determining the gas fraction of the medium and fourth a signal processing unit for processing the signals of the different sensors. Such is, however, a complex and costly device.

SUMMARY

It is, consequently, an object of the present invention to provide a method and a corresponding measuring arrangement for reliable, continuous measuring of the fat fraction of milk also in the case of variable solids fractions and variable gas content.

The object is achieved according to the invention by the method as defined in independent claim 1 and the measuring arrangement as defined in independent claim 8.

The method of the invention for continuous determining of fat content of milk having variable solids fractions and flowing with variable gas content in a pipeline, comprises:
ascertaining a value for velocity of sound and an average density value for milk flowing in the pipeline based on eigenfrequencies of at least two bending oscillation wanted modes of measuring tubes of a densimeter arranged in the pipeline;
ascertaining a value for static pressure in the pipeline by means of a pressure sensor connected to the pipeline;
ascertaining a value for gas volume fraction based on the value for the velocity of sound, the value for the average density and the value for the pressure;
ascertaining a value of density of milk flowing in the pipeline without gas content based on the value for the average density and based on the value for the gas volume fraction;
ascertaining a value for permittivity of milk flowing in the pipeline based on at least one measuring of propagation velocity and/or absorption of microwaves in the milk by means of a microwave sensor arranged in the pipeline; and
calculating fat fraction based on the value of the density of the milk flowing in the pipeline without gas content and the value for the effective permittivity.

In a further development of the invention, the milk is modeled as a three components system, wherein the components comprise fat, water and fat-free solids.

In a further development of the invention, the solids comprise proteins and carbohydrates, among these especially lactose.

In a further development of the invention, the density of the milk flowing in the pipeline without gas content is modeled as a function, for example, a linear function, of concentration of the components contained in the milk with density values of pure components as weighting factors; wherein effective permittivity of milk flowing in the pipeline is modeled taking into consideration gas content as a function of concentration of the components contained in the milk and permittivity values of the pure components; and wherein concentration of the components is ascertained, which lead to the ascertained values of the density and the effective permittivity of the milk.

In a further development of the invention, the determining of the permittivity occurs in the presence of at least one frequency above 1 GHz, especially above 2 GHz, for example, at 2.45 GHz.

In a further development of the invention, the method further includes measuring temperature of milk flowing in the pipeline; and ascertaining temperature dependent values for density and/or permittivity of the components contained in the milk.

In a further development of the invention, the densimeter comprises a Coriolis mass flowmeter, wherein the method further comprises:
ascertaining mass flow, volume flow and/or fat flow in the pipeline.

The measuring arrangement of the invention for determining fat content of milk in a pipeline, especially with the method as claimed in one of the preceding claims, comprises:

a densimeter having at least one oscillatable measuring tube for ascertaining a density measured value and a sound velocity measured value of a medium contained in the measuring tube based on at least wanted mode eigenfrequencies of at least two bending oscillation wanted modes;

a pressure sensor for measuring an absolute pressure of a medium;

a microwave sensor for ascertaining absorption and/or propagation velocity of microwave signals in a medium; and a computer unit for calculating fat content based on measured values of the densimeter, the pressure sensor and the microwave sensor.

In a further development of the invention, the densimeter, the pressure sensor and the microwave sensor are installed in the pipeline.

In a further development of the invention, the densimeter comprises a Coriolis mass flowmeter.

BRIEF DESCRIPTION OF THE DRAWINGS

The invention will now be explained in greater detail based on the example of an embodiment shown in the drawing. The figures of the drawing show as follows:

FIG. 2 shows a more detailed flow diagram of an example of an embodiment of a first subprocess of the method of the present disclosure;

DETAILED DESCRIPTION

Figures 1, 2A, 2B, 2C, 3:
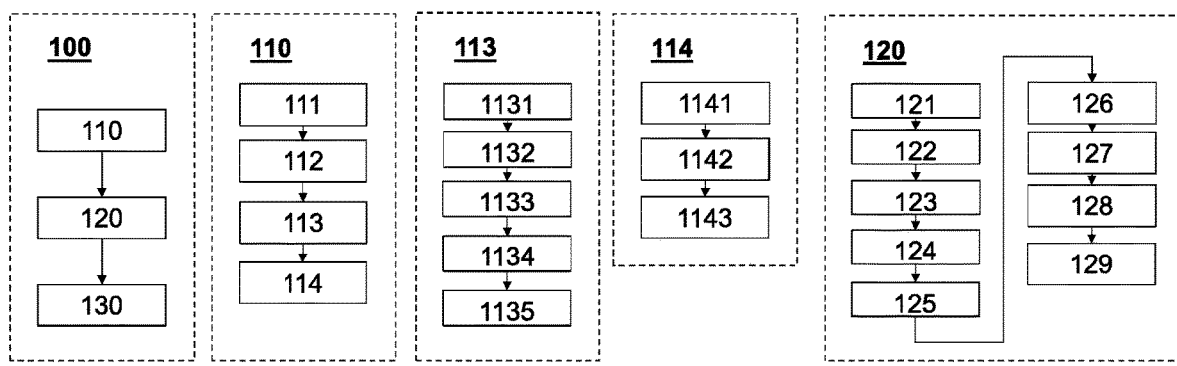
FIG. 1 shows a flow diagram of an example of an embodiment of the method of the present disclosure.
FIG. 3 shows a more detailed flow diagram of an example of an embodiment of a second subprocess of the method of the present disclosure.

The components of milk can essentially be summarized in four groups, namely water, fat, protein and carbohydrates, wherein the latter comprise, for example, more than 95% lactose and small portions of glucose and galactose. Additionally, as a function of physical process conditions, especially as a function of existing flow conditions, air inclusions can be present in the form of microbubbles, which are to be taken into consideration in an analysis. The following table presents, by way of example, the physical properties of the components and air:

| | density $\rho$ [g/cm$^2$] @ 20° C. | relative permittivity $\varepsilon'(f = 2.45$ GHz$)$ @ 20° C. |
|---|---|---|
| water | 0.998 [1] | 78 [2] |
| fat | 0.931 [1] | 2.6 [2] |
| protein | 1.451 [1] | 1.6 [2] |
| carbohydrates (lactose) | 1.545 [1] | 1.9 [2] |
| air | 0.0012 | 1.0 |

With the help of these variables, the effective density and permittivity of the mixture, in each case, as a function of fractions $a_i$ of the components can be given as:

$$\rho_{milk\ with\ air} = f((1-a_{air})a_{water}, (1-a_{air})a_{fat}, (1-a_{air})a_{SNF}, a_{air})$$

$$\Sigma'_{eff} = f((1-a_{air})a_{water}, (1-a_{air})a_{fat}, (1-a_{air})a_{SNF}, \alpha)$$

The air fraction $a_{air}$ can be ascertained by means of the densimeter and the auxiliary variable, pressure, and is taken into consideration in the equations as a known parameter. These relationships hold naturally also in the case of processes, in which air fractions are, process related, not present ($a_{air}=0$).

Since both the density as well as also the permittivity of carbohydrates and proteins are almost the same, these can essentially be combined without problem as one component, fat-free solids (i.e. Solids-NonFat (SNF)) and be taken into consideration by calculation with average density and permittivity, which results using a typical mixing proportion of the two components in milk. In the case of cow milk, this would be according to Wikipedia approximately 58% carbohydrates (96% of which is lactose) and 42% proteins.

The average density can essentially be calculated as a weighted average of the individual densities.

A typical mixing equation, in order to determine $\varepsilon'_{eff}$ in a mixture of a plurality of components, is the Bruggemann formula:

$$\frac{\epsilon_{MG} - \epsilon_h}{\epsilon_{MG} + 2\epsilon_h} = \sum_{n=1}^{N} f_n \frac{\epsilon_n - \epsilon_h}{\epsilon_n + 2\epsilon_h}$$

In such case:

$\varepsilon_{MG}$: $\varepsilon'_{eff}$
$\varepsilon_h$: permittivity of the matrix phase (water)
$\varepsilon_n$: permittivity of the additives (fat, SNF, air)
$f_n$: volume fractions of the various components
[formula taken from V Markel—Introduction to the Maxwell Garnett Approximation, Journal of the Optical Society of American A]

There results:

$$\rho_{milk} = f(a_{water}, a_{fat}, a_{SNF}) \quad (Eq1)$$

$$\Sigma'_{eff} = f((1-a_{air})a_{water}, (1-a_{air})a_{fat}, (1-a_{air})a_{SNF}, a_{air}) \quad (Eq2)$$

wherein $a_{air}$ is the volume fraction of the gas content.

A third equation results from the sum of the volume fractions:

$$a_{water} + a_{fat} + a_{SNF} = 1 \quad (Eq3)$$

There results three equations with three unknowns, with which the determining of the fractions of water, fat, and fat-free solids is possible without other assumptions.

In particular, density and permittivity depend on temperature and the permittivity on the measuring frequency. A temperature measurement for taking into consideration the temperature dependencies of the material properties in the solution of the above system of equations enables a desired accuracy.

As shown in FIG. 1, the method 100 begins with a first step 110 of determining the density of the milk $\rho_{milk}$ free of air fractions. This is performed by ascertaining the average density, thus, the density of the milk with air $\rho_{milk\ with\ air}$, ascertaining the air fraction $a_{air}$ and correcting the density by removing the air fraction.

In a second step 120, there follows the determining of the effective permittivity $\Sigma'_{eff}$, this being accomplished by measuring the propagation properties of an electromagnetic wave in the milk.

In a third step 130, the system of equations Eq1, Eq2, Eq3 is solved, in order to determine the fat fraction and, in given cases, the fractions of other components.

As shown in FIG. 2a, the step 110 is subdivided into steps as follows:

In a step 111, there occurs the determining of the eigenfrequencies of the $f_1$-bending oscillation mode and the $f_3$-bending oscillation mode of a Coriolis mass flow measuring transducer, which here is also applied for density measurement. For this, the $f_1$-bending oscillation mode and the $f_3$-bending oscillation mode especially can be simultaneously excited. By maximizing the ratio of the oscillation amplitude to the mode specific excitation power by varying the excitation frequencies, the sought eigenfrequencies can be ascertained.

Based on the ascertained eigenfrequencies $f_i$, in a step 112, preliminary density values $\rho_1$ and $\rho_3$ are determined as:

$$\rho_i = c_{0i} + c_{1i}\frac{1}{f_i^2} + c_{2i}\frac{1}{f_i^4},$$

wherein $c_{0i}$, $c_{1i}$, and $c_{2i}$, are mode dependent coefficients.

In a step 113, there occurs the determining of the velocity of sound of the gas-containing liquid and, in given cases, a correction term for the density measurement.

Then, in a step 114, by means of the velocity of sound and a pressure measurement value, a gas volume fraction $a_{air}$ is calculated, and the density of the milk minus the air is calculated, such as explained in greater detail below.

As shown in FIG. 2b, step 113 includes for determining the correction term, firstly, in a step 1131, calculating the ratio V of the preliminary density values, thus, for example, division of the preliminary density values $\rho_1$ and $\rho_3$ to form $V:=\rho_1/\rho_3$.

Then, in a step 1132, a value of the velocity of sound c is determined, which with the measured eigenfrequencies $f_1$ and $f_3$ of the bending oscillation modes leads in the following equation to the observed ratio V of the preliminary density values:

$$\frac{\left(1 + \frac{r}{\left(\frac{g \cdot c}{f_1}\right)^2 - b}\right)}{\left(1 + \frac{r}{\left(\frac{g \cdot c}{f_3}\right)^2 - b}\right)} = V$$

wherein r is, for instance, 0.84, b=1 and g is a measuring tube dependent, proportionality factor between velocity of sound and resonant frequency, which can, for example, assume a value of 10/m. The value of the velocity of sound, which fulfills the above equation, is the sought value for the velocity of sound of the gas-containing liquid.

Based on the ascertained sound velocity value, then in step 1133 of the method in FIG. 2b a mode specific correction term $K_i$ for the resonator effect can be calculated:

$$K_i := \left(1 + \frac{r}{\left(\frac{g \cdot c}{f_i}\right)^2 - 1}\right).$$

A density value for the air containing milk $\rho_{milk\ with\ air}$ can, finally, be calculated in step 1134 as:

$$\rho_{milk\ with\ air} = \frac{\rho_i}{K_i} \quad (M1)$$

The determining of air fraction and the calculating of the density of the air-free milk in step 114 is shown in FIG. 2c in greater detail and is based on the following relationship between the velocity of sound of a gas-containing liquid and additional parameters:

$$c = \left[\frac{\alpha}{c_{air}^2} + \frac{(1-a_{air})^2}{c_{milk}^2} + \frac{\alpha(1-a_{air})\cdot\rho_{milk}}{\gamma \cdot p}\right]^{-\frac{1}{2}} \quad (C1)$$

In such case, $a_{air}$ is the air volume fraction, $c_{air}$ the velocity of sound in air, $c_{milk}$ the velocity of sound in milk without air, $\gamma$ the adiabatic coefficient for air, p the current pressure of the air-containing milk and $\rho_{milk}$ the density of the milk without air.

The density of the air-containing milk results as the weighted sum of the individual densities. Insofar as the density of air at standard pressure lies, for instance, three orders of magnitude below the density of pure milk, and the volume fraction of the air lies in the order of magnitude of a few %, the density of milk with air can be estimated as follows:

$$\rho_{milk\ with\ air} = \rho_{milk}(1-a_{air}) + \rho_g \alpha$$

$$\rho_{milk\ with\ air} \approx \rho_{milk}(1-a_{air}) \quad (M2)$$

Therewith, the equation C1 for the velocity of sound can be written as:

$$c = \left[\frac{a_{air}}{c_{air}^2} + \frac{(1-a_{air})^2}{c_{milk}^2} + \frac{a_{air}\rho_{milk\ with\ air}}{\gamma p}\right]^{-\frac{1}{2}}$$

By neglecting the square term in $a_{air}$, there results:

$$c = \left[\frac{a_{air}}{c_{air}^2} + \frac{1-2a_{air}}{c_{milk}^2} + \frac{a_{air}\rho_{milk\ with\ air}}{\gamma p}\right]^{-\frac{1}{2}}$$

Solving for $a_{air}$ gives for the air volume fraction a value of $$a_{air} = \frac{\frac{1}{c_{milk\ with\ air}^2} - \frac{1}{c_{milk}^2}}{\frac{1}{c_{milk\ with\ air}^2} - \frac{2}{c_{milk}^2} + \frac{\rho_{milk\ with\ air}}{\gamma p}}$$

Actually the denominator is, in the pressure range relevant for milk processing, essentially dominated by the third term, so that the following approximation results:

$$a_{air} \approx \frac{\gamma p}{\rho_{milk\ with\ air}} \cdot \left(\frac{1}{c_{milk\ with\ air}^2} - \frac{1}{c_{milk}^2}\right) \quad (A1)$$

Here, a reference value can be used for the velocity of sound $c_{milk}$ in pure milk without air.

As shown in FIG. 2c, for determining the air fraction in step 1141 a pressure value of the gas-containing liquid is ascertained, which reigns in the milk at the point in time of measuring the eigenfrequencies $f_1$ and $f_3$, in order that with equation M1 the density $\rho_{milk\ with\ air}$ as well as with equation C1 the velocity of sound of the air-containing milk $c_{milk\ with\ air}$ can be ascertained.

For the adiabatic coefficient γ, it holds that:

$\gamma=c_p/c_v=(f+2)/f$, wherein f is the number of molecular degrees of freedom of the gas, which amounts at room temperature, for example, to 1.4 for nitrogen and dry air.

In a step 1142, then based on the pressure measured value, the above ascertained density of the air-containing milk $\rho_{milk\ with\ air}$ as well as the above ascertained velocity of sound of the air-containing milk $c_{milk\ with\ air}$, the air volume fraction $a_{air}$ is calculated with equation A1.

In a step 1143, there follows the calculating of the sought density $\rho_{milk}$ for the air-free milk:

$$\rho_{milk} \approx \rho_{milk\ with\ air} \frac{1}{1 - a_{air}} \quad (M3)$$

This provides the first measured variable, in order to solve the system of equations Eq1, Eq2, Eq3.

The second step 120 will now be described, in which the second measured variable, namely the relative permittivity, is ascertained.

Basis for such is a measurement 121 of the propagation properties of an electromagnetic wave (amplitude and phase of the received signal relative to the transmitted signal) within the medium in the pipeline between a transmitting antenna and a receiving antenna separated with a separation d. This measurement 121 can be performed with electromagnetic waves of different frequency f, so that a transfer function in the frequency domain S(f) within a band from e.g. 2 GHz-4 GHz is ascertained at 122.

In practical measuring systems, the measured spectrum S(f) does not contain exclusively the (medium dependent) propagation properties in the distance between the transmitting- and receiving antennas, but, instead, also the attenuation and phase rotation of the antennas, connection cable as well as transition locations. Added to this, in given cases, are the influences of multiple reflections in the region of the connection cable. By suitable reference measurements, these influences can be largely characterized and, as a result, measurements compensated at 123, so that only the relevant part of the transfer function between transmitting- and receiving antenna remains.

From the transfer function S(f) using inverse Fourier transformation, the impulse response in the time domain can be calculated at 124. Because of the measuring of a limited band region, then also present here is the pulse response of the system to excitation with a band limited impulse, whose form results from the form of the window function applied for the inverse Fourier transformation. From the position of the maximum of this delayed impulse relative to the time axis, the group propagation time $\tau_g$ within the measured, band limited region can be ascertained at 125. From this, in simple manner, the propagation velocity of the signal can be estimated at 126:

$$c = \frac{d}{\tau_g}$$

In many polar media, dispersion occurs (dependence of the permittivity and therewith the propagation velocity on the frequency of the electromagnetic wave). For this reason, the above estimated, average propagation time in the sense of a group propagation time is only limitedly suitable for direct determining of the media properties. In order to enable a precise measuring, the phase response can be utilized by calculating in the measured frequency band the phase travel time as a function of frequency at 127: $\varphi=\arg(S(f))$ $$\tau_{ph}(f) = -\frac{d\varphi(f)}{df}$$

The ambiguity of the phase response, describable by a whole number n in $\varphi_{real}=\varphi_{measured}+n\cdot 2\pi\tau_{ph}\tau_{gr}$, can be removed by selecting n such that the deviation between $\tau_{ph}$ and $\tau_{gr}$ is minimum. In this way, now the phase response and, by $$c(f) = \frac{d}{\tau_{ph}(f)}$$

also the exact response of the propagation velocity versus frequency are determinable at 128. The behavior of the attenuation d is directly known from the amplitude response of S(f).

From the now known behaviors of c and α as expressed by the following two equations, in 129, these can be directly converted into the physical variable of the complex valued permittivity of the medium: $\epsilon^*=\epsilon'+j\ \epsilon''$ $$c = \left[\frac{\mu\epsilon_0\epsilon'}{2}\left[\sqrt{1+\left(\frac{\epsilon''}{\epsilon'}\right)^2}+1\right]\right]^{-\frac{1}{2}}$$

$$\alpha = \omega\left[\frac{\mu\epsilon_0\epsilon'}{2}\left[\sqrt{1+\left(\frac{\epsilon''}{\epsilon'}\right)^2}-1\right]\right]^{\frac{1}{2}}$$

where:
ω: angular frequency (ω=2πf)
μ: permeability, $\mu=\mu_0\mu_r$
$\mu_0$: magnetic field constant, $$\mu_0 = 4\pi \cdot 10^{-7} \frac{n}{a^2}$$

$\mu_r$: relative permeability
$\epsilon_0$: electrical field constant, $$\epsilon_0 \approx 8{,}854 \cdot 10^{-12} \frac{As}{Vm}$$

The values for $\epsilon^*$ and $\epsilon'$ determined from the measuring can now be utilized in equation Eq2, either by using the value at an earlier defined measuring frequency or by processing the total measurement data vector in Eq2.

Based on the above, everything is ready, in order to solve the system of equations Eq1, Eq2, Eq3 and, thus, to determine the fractions of the components in the milk, especially the fat fraction.

Figure 4:
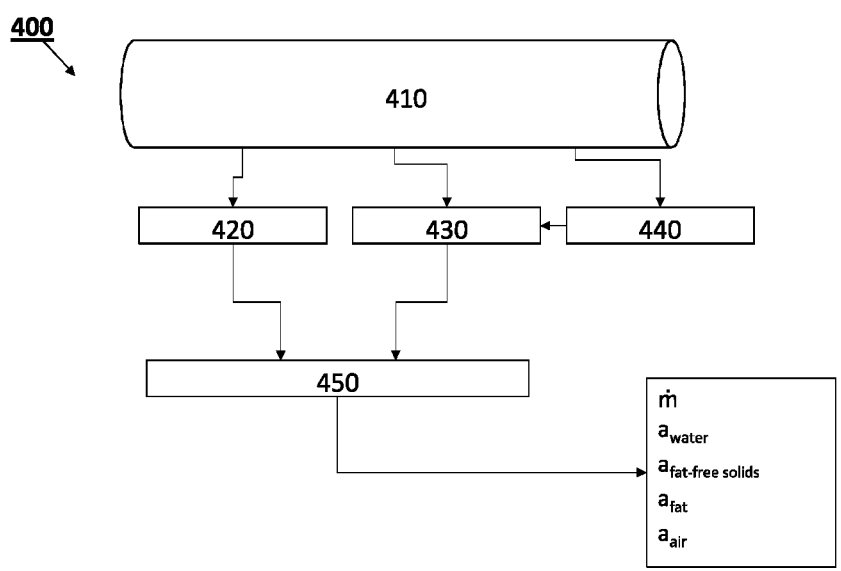
FIG. 4 shows a schematic view of an example of an embodiment of a device of the present disclosure.

FIG. 4 shows, finally, a measuring arrangement 400 of the invention for determining the milk fat fraction, especially by means of the method of the invention. The measuring arrangement 400 includes measuring devices installed in a pipeline 400, namely a microwave sensor 420, a Coriolis-mass flowmeter 430 for registering density and mass flow of a medium flowing in the pipeline 410, especially a Coriolis-mass flowmeter with two bent measuring tubes, as well as an absolute pressure sensor 440, which has a measured value output, which is connected to an auxiliary signal input of the Coriolis mass flowmeter. The measuring arrangement 400 includes, additionally, a computer unit 450, which is connected to the signal outputs of the microwave sensor 420 and the Coriolis-mass flowmeter 430. The microwave sensor 420 is adapted, based on signal travel times, to register permittivity values and/or absorption of the medium flowing in the pipeline and to output such to the computer unit 450. The Coriolis-mass flowmeter 430 is adapted to ascertain, besides the mass flow $\dot{m}$ (m-dot), the density, the air fraction $a_{air}$ and the media temperature T and to output these to the computer unit 450. The computer unit 450 is adapted, based on these input variables, to ascertain the composition of the medium flowing in the pipeline and to output such under the assumption that the medium is milk.

The invention claimed is:

1. A method for determining a fat content of milk, wherein the milk has variable solids fractions and flows with a variable gas content in a pipeline, the method comprising:
   arranging a densimeter in the pipeline and flowing the milk through the densimeter;
   determining a first eigenfrequency of a first bending oscillation mode of the densimeter and a second eigenfrequency of a second bending oscillation mode of the densimeter;
   calculating a velocity of sound in the milk and calculating an average density for the milk based on the first and second eigenfrequencies;
   measuring a static pressure in the pipeline using a pressure sensor connected to the pipeline;
   calculating a gas volume fraction of the milk based on the velocity of sound in the milk, the average density, and the static pressure;
   calculating a density of the milk without gas content based on the average density and based on the gas volume fraction;
   measuring a propagation velocity and/or an absorption of microwaves in the milk using a microwave sensor arranged in the pipeline and calculating an effective permittivity of the milk from the propagation velocity and/or the absorption; and
   calculating a fat fraction of the milk based on the density of the milk without gas content and on the effective permittivity of the milk.

2. The method as claimed in claim 1, further comprising: modeling the milk as a three component system of fat, water, and fat-free solids.

3. The method as claimed in claim 2, wherein the fat-free solids include proteins and carbohydrates.

4. The method as claimed in claim 3, further comprising: calculating a concentration of each of the three components of fat, water, and fat-free solids;

modeling the density of the milk without gas content as a function of each of the concentration of each of the components of fat, water, and fat-free solids using density values of the respective component as weighting factors;
modeling the effective permittivity of the milk using the gas volume fraction of the milk, the concentration of each of the components of fat, water, and fat-free solids, and permittivity values of the respective components.

5. The method as claimed in claim 4, further comprising: measuring a temperature of the milk; and
calculating temperature dependent values for density and/or permittivity of the components contained in the milk.

6. The method as claimed in claim 4, wherein the densimeter includes a Coriolis mass flowmeter, the method further comprising:
   calculating at least one of the following: a mass flow of the milk, a volume flow of the milk, a fat flow of the milk, a fat-free solids flow of the milk, and a water flow of the milk in the pipeline.

7. The method as claimed in claim 1, wherein the microwaves include at least one frequency above 1 GHz.

8. A measuring arrangement for determining a fat content of milk in a pipeline, comprising:
   a densimeter having at least one oscillatable measuring tube and configured to determine a first eigenfrequency of a first bending oscillation mode and a second eigenfrequency of a second bending oscillation mode;
   a pressure sensor for measuring a static pressure in the pipeline;
   a microwave sensor for ascertaining a propagation velocity and/or an absorption of microwave signals in the milk; and
   a computer unit for calculating the fat content of the milk, wherein the computer unit is configured to:
      calculate a velocity of sound in the milk and calculate an average density for the milk based on the first and second eigenfrequencies;
      read the static pressure in the pipeline using the pressure sensor;
      calculate a gas volume fraction of the milk based on the velocity of sound in the milk, the average density, and the static pressure;
      calculate a density of the milk without gas content based on the average density and based on the gas volume fraction;
      measure the propagation velocity and/or the absorption of microwaves in the milk using the microwave sensor;
      calculate an effective permittivity of the milk from the propagation velocity and/or absorption; and
      calculate a fat fraction of the milk based on the density of the milk without gas content and on the effective permittivity.

9. The measuring arrangement as claimed in claim 8, wherein the densimeter, the pressure sensor, and the microwave sensor are installed in the pipeline.

10. The measuring arrangement as claimed in claim 8, wherein the densimeter includes a Coriolis mass flowmeter.

* * * * *